United States Patent
Tikare

(10) Patent No.: US 7,094,920 B2
(45) Date of Patent: Aug. 22, 2006

(54) STEREOSELECTIVE SYNTHESIS OF 2-HYDROXY-4-PHENYLBUTYRIC ACID ESTERS

(75) Inventor: Raveendra Khandurao Tikare, Thane (IN)

(73) Assignee: Fermenta Biotech Limited, (IN)

( * ) Notice: Subject to any disclaimer, the term of this patent is extended or adjusted under 35 U.S.C. 154(b) by 296 days.

(21) Appl. No.: 10/719,660

(22) Filed: Nov. 21, 2003

(65) Prior Publication Data

US 2004/0236141 A1 Nov. 25, 2004

Related U.S. Application Data

(63) Continuation of application No. PCT/IB02/01689, filed on May 16, 2002.

(30) Foreign Application Priority Data

May 21, 2001 (GB) ................. 0112322.3

(51) Int. Cl.
C07C 69/76 (2006.01)
(52) U.S. Cl. ..................... 560/103
(58) Field of Classification Search ......... 560/103
See application file for complete search history.

(56) References Cited

U.S. PATENT DOCUMENTS 5,302,746 A * 4/1994 Koono et al. .......... 560/205
5,552,317 A   9/1996 Houng et al.
5,959,139 A * 9/1999 Kurauchi et al. ........ 560/193

FOREIGN PATENT DOCUMENTS

| EP | 0759424 A1 | 2/1997 |
|---|---|---|
| JP | 3200739 | 9/1991 |
| JP | 9-118646 | 5/1997 |
| WO | WO-00/17228 A2 | 3/2000 |
| WO | WO-02/094761 A1 | 11/2002 |

OTHER PUBLICATIONS

Effenberger, Franz, et al., "Stereoselective synthesis of 3-amino-4,5-dihydroxyaldehydes—a novel preparation of N-acetyl-L-daunosamine", *Tetrahedron: Asymmetry*, vol. 11, (2000),1085-1095.
Göehring, W., et al., "Synthesis of the HIV-Proteinase Inhibitor Saquinavir: A Challenge for Process Research", *Chimia*, Aarau, CH, vol. 50, No. 11, (1996),532-537.
Iwasaki, Genji, et al., "A Practical and Diastereoselective Synthesis of Angiotensin Converting Enzyme Inhibitors", *Chemical & Pharmaceutical Bulletin*, 37(2), (1989),280-283.
Kakeya, H., et al., "Preparation of Optically Active Alpha-Hydroxy Acid Derivatives by Microbial Hydrolysis of Cyanohydrins", *Agricultural and Biological Chemistry*, 55(7), (1991),1877-1881.
March, J., "Chapter 6-9 Alcoholysis of Nitriles", In: *Advanced Organic Chemistry—Reactions, Mechanisms, and Structure*, (Third Edition, 1985, John Wiley & Sons, Inc.),792-793.
Minamikawa, H., et al., "Asymmetric Hydrocyanation of Aldehydes Using Chiral Titanium Reagents", *Bulletin of the Chemical Society of Japan*, vol. 61, No. 12, (1988),4379-4383.
Urbach, H., et al., "A Favourable Diastereoselective Synthesis of N-(1-S-Ethoxycarbonyl-3-Phenylpropyl)-S-Alanine", *Tetrahedron Letters*, 25(11), (1984),1143-1146.
Wang, Yi-Fong, et al., "Lipase-Catalyzed Irreversible Transesterification Using Enol Esters: Resolution of Cyanohydrins and Syntheses of Ethyl (R)-2-Hyrdoxy-4-Phenylbutyrate and (S)-Propranolol", *Tetrahedron Letters*, 30(15), (1989),1917-1920.
Yanagisawa, Hiroaki, et al., "Angiotensin-Converting Enzyme Inhibitors: Perhydro-1,4-thiazepin-5-one Derivatives", *J. Med. Chem.*, vol. 30, (1987),1984-1991.

* cited by examiner

*Primary Examiner*—Kamal A. Saeed
*Assistant Examiner*—Susannah L. Chung
(74) *Attorney, Agent, or Firm*—Schwegman, Lundberg, Woessner & Kluth, P.A.

(57) ABSTRACT

A process is described for the stereospecific preparation of an ester of formula (I): wherein * signifies the (R) stereoisomer; $R^1$ is selected from $C_{1-6}$ alkyl, preferably ethyl; and $R_2$ is hydrogen, a protecting group or a leaving group which process comprises reaction of a nitrile of formula (II): wherein * signifies the (R) stereoisomer; and Ph is the phenyl group $C_6H_5$ with a solution of an inorganic acid in an alcohol and optional conversion of the compound of formula (I) wherein $R^2$ is H so prepared to any other desired compound of formula (I) by standard methods in the art. The compounds of formula (I) are chiral esters, useful as intermediates in the synthesis of the family of acetylcholine esterase (ACE) inhibitors known as "prils", such as lisinopril, cilazapril, enalapril, benazepril, ramipril, delapril, enalaprilat, imidapril, spirapril, trandolapril and others.

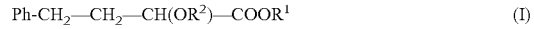

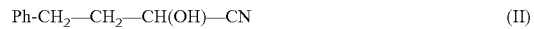

17 Claims, No Drawings

STEREOSELECTIVE SYNTHESIS OF 2-HYDROXY-4-PHENYLBUTYRIC ACID ESTERS

RELATED APPLICATIONS

This application is a continuation under 35 U.S.C. 111(a) of International Application No. PCT/IB02/01689 filed May 16, 2002 and published in English as WO 02/094761 A1 on Nov. 28, 2002, which claimed priority from United Kingdom Application No. 0112322.3 filed May 21, 2001, which applications and publication are incorporated herein by reference.

The present invention relates to a process for the synthesis of chiral compounds, and in particular chiral esters, for use as intermediates in the synthesis of the family of acetylcholine esterase (ACE) inhibitors known as 'prils'.

The 'prls' have the general formula (A):

wherein R' is hydrogen or $C_1$–$C_2$ alkyl and R" is selected from a large number of possible moieties. Examples of 'prils' include lisinopril, cilazapril, enalapril, benazepril, ramipril, delapril, enalaprilat, imidapril, spirapril, trandolapril and others.

These 'pril' compounds are chiral compounds, only one of their diastereomers being pharmacologically active. It is therefore necessary to isolate and purify the active diastereomer, rather using a racemic mixture, for pharmaceutical/medical applications.

Typically, separation of diastereomers is carried out by preferential crystallisation, for example as described in U.S. Pat. No. 5,616,727. However, the yields of such crystallisations are often low and, indeed, the yield from the process used in U.S. Pat. No. 5,616,727 was only 68%.

Alternatively, a stereochemical synthesis may be used, wherein various intermediates used in the preparation of the 'prils' are, in turn, prepared in chiral form, which results in a predominance of the desired diastereomer in the final 'pril' product. However, such chiral syntheses are complex and the yields are also unsatisfactory.

The present invention relates to an improved, stereospecific process for the synthesis of an intermediate for making 'pril' compounds. This intermediate can be converted to the required 'pril' isomer, or any other desired end-product, without loss of stereospecificity. The intermediate of interest is an ester of formula (I):

wherein * signifies the (R) stereoisomer;
$R^1$ is selected from $C_{1-6}$ alkyl, preferably ethyl; and
$R^2$ is hydrogen, a protecting group or a leaving group.

Suitable leaving groups $R^2$ include p-toluene sulphonyl (tosyl), methane sulphonyl chloride (mesyl), trifluoromethane sulphonyl (triflic), and p-nitrobenzene sulphonyl.

Suitable protecting groups $R^2$ include tert-butyl dimethyl siliyl (TBDMS), TMS, BOC and the like.

One method of stereospecific synthesis involves the conversion of the compound (R)-2-hydroxy-4-phenylbutyronitrile having the formula (II):

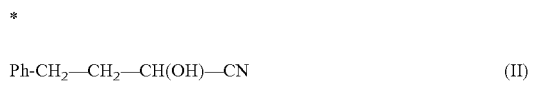

wherein * signifies the (R) stereoisomer; and Ph is the phenyl group $C_6H_5$ to the corresponding ester of formula (I).

In Tet. Lets. 30 (15) 1917–20 (1989) is disclosed the above process to produce a compound of formula (I) wherein $R^2$ is H and $R^1$ is ethyl. However, the method described involves a three-stage process, resulting in a yield of only 78%, based on the nitrile of formula (II). The three process steps are: (i) treating the nitrile (II) with dihydopyran in pyridinium p-toluene sulphonate to prepare the THP derivative; (ii) hydrolysing the nitrile group with sodium hydroxide; and, finally, treating the resulting acid with anhydrous ethanol and a catalytic amount of concentrated sulphuric acid.

We have therefore looked at the possibility of using alternative methods of synthesising this ester, but none of these appeared to provide the desired combination of high ee (eg 97–98%); conomic reaction time; acceptable yields (eg >80%); and overall ease of handling and commercial viability of the process.

Instead, we have surprisingly found that, by careful selection of novel reaction conditions and reagents, we can obtain the desired ee in high yields and under commercially-acceptable conditions, involving a so-called 'one-pot' reaction, in which the reaction appears to go in one step, without the addition of further reagents or reactants, but with the formation of an unstable intermediate that need not be isolated but converts in situ to the desired compound of formula (I).

The novel one-pot reaction according to this invention involves reacting the nitrile of formula (II) with an alcoholic solution of an inorganic acid, such as sulphuric acid or hydrochloric acid, to give the ester of formula (I) via an in situ conversion.

There is therefore provided a process for the stereospecific preparation of an ester of formula (I):

wherein * signifies the (R) stereoisomer;
$R^1$ is selected from $C_{1-6}$ alkyl, preferably ethyl; and
$R^2$ is hydrogen, a protecting group or a leaving group which process comprises reaction of a nitrile of formula (I):

wherein * signifies the (R) stereoisomer; and Ph is the phenyl group $C_6H_5$ with a solution of an inorganic acid in an alcohol and optional conversion of the compound of formula (I) wherein $R^2$ is H so prepared to any other desired compound of formula (I) by standard methods known to those skilled in the art.

Accordingly, the present invention further provides a process for preparing a compound of formula (I), which process comprises reaction of an intermediate imine of formula (III):

in which $R^2$ is as defined in formula (I); and X is the anion of an inorganic acid, such as sulphate or halide, preferably halide, more preferably chloride, with an alcohol of formula $R^1OH$, in which $R^1$ is as defined in formula (I) and * signifies the (R) stereoisomer.

It is preferred that $R^1$ is $C_1$–$C_4$ alkyl, for example methyl, ethyl, n-propyl, iso-propyl, n-butyl, iso-butyl or tert-butyl. Accordingly, ethanol is the preferred alcohol. Conveniently, the alcoholic solution of the acid is prepared by bubbling dry, gaseous add into absolute alcohol. Preferable, the solution comprises at least 4–5% w/v of acid (gas), more preferably >7% w/v, such as in the range of from 7–15% w/v, based on grams of acid per 100 ml of alcohol.

It is preferred that the alcohol/acid solution be as anhydrous as possible, in order to ensure that the ester is formed in preference to the corresponding acid. The reaction may be carried out at a temperature in the range of from 0 to 80° C., such as at reflux temperature of the reaction mixture, at atmospheric pressure. For example, using the ethanol/HCl, the reaction may be carried out at 70–85° C. over a period in the range of from 12 to 20 hours, such as at 75–80° C. over a period of 15 hours, or for 2 hours at 10–15° C. followed by refluxing for 15 hours, all at atmospheric pressure. The skilled chemist will be able to adjust the temperature/pressure/reaction period factors appropriately.

The ratio of nitrile of formula (II): acid/alcohol solution is in the range of from 1:6 to 1:10, preferably about 1:8, by volume.

The yield of this reaction is about 80% of theoretical with an enantiomeric excess (ee), based on optical rotation, of the (R) isomer of about 97%.

The present invention therefore further provides an ester of formula (I), in particular, an ester of formula (I) comprising at least 97% of the (R) isomer, whenever prepared by a process according to this invention; and such a compound (I) for use in, or whenever used in, the preparation of a stereospecific 'pril' of formula (A).

Furthermore, there is provided a method for the preparation of a stereospecific 'pril' of formula (A), which method comprises preparation of an ester of formula (I) by a process according to this invention; and a stereospecific 'pril' of formula (A), whenever prepared by such a process.

The invention will now be described in more detail with reference to the following non-limiting examples.

EXAMPLE

Preparation of (R)-2-Hydroxy-4-phenyl butyric acid

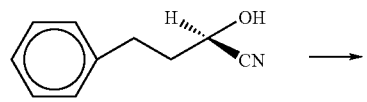

(R)-isomer (II)

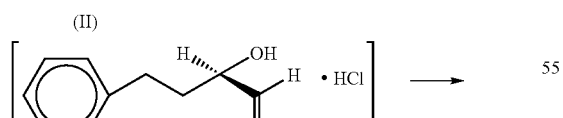

(III)

-continued

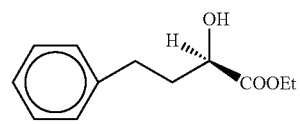

(R)-isomer (I)

(a) Preparation of Alcoholic HCl (g)

To 1 kg of common salt (NaCl) was added 250 ml of concentrated sulphuric acid, dropwise at room temperature. The hydrogen chloride gas evolved was first passed through a trap containing concentrated sulphuric acid to dry it and then passed with stirring into absolute alcohol (2 l) which was kept at 0–5° C. The process was carried out for 4–6 hours until the required strength was obtained.

(b) Preparation of Title Compound

To (R)-2-hydroxy-4-phenyl-butyronitrile ((II), 250 g, 1.55 M) was added absolute alcohol (2 l) which contained at least 7% w/v of dry hydrogen chloride gas at 10–15° C. The mixture was stirred for 2 hours at the same temperature. This was carried out to allow confirmation of the conversion of the nitrile to the corresponding imine hydrochloride. After this, the reaction mass was refluxed at 75–80° C. The reaction was monitored using TLC and after 15 hours was found to be complete.

The alcohol was removed from the reaction mass in vacuo at 55–60° C. The resulting residue was taken in water (1 l) and extracted with dichloromethane (500 ml×2). The collective organic phases were dried over anhydrous sodium sulphate and concentrated in vacuo to yield a reddish, thick liquid. This was vacuum-distilled to obtain the desired product in 78–80% yield (of theoretical), as a colourless liquid.

The whole process can be summarized as follows:

| Substrate | in Ethanolic HCl | HCl concentration | T mp | Tim | Yield | Purity by HPLC |
|---|---|---|---|---|---|---|
| (R)-2-Hydroxy-4-phenylbutyronitrile | 1:8 by volume | 7–15% w/v | 75–80° C. | 15 hrs | 78–80% of theoretical | 98% |

Analytical Data:

$^{20}[\alpha]_D$: −10 at 100% concentration (solvent free).

Reported $^{20}[\alpha]_D$: −10±1 at 100% concentration (solvent free).

Boiling point: 125–127° C. at 1 mm Hg to 2 mm Hg vacuum; 120° C. at 1.5 mm

NMR (Varian$^{RTM}$ 60 MHz): (CCl$_4$, TMS) 7.3 (S, 5 H), 3.8–4.3 (m, 3 H), 2.5–2.8 (t, 3 H), 1.4–2 (m, 2 H), 1–1.3 (t, 3 H)

Density: 1.0751

Refractive index: 1.502

HPLC 1: Column C$_{18}$ (250 mm×4.6 mm×5μ); mobile phase: methanol:H$_2$O (80:20); wavelength: 210 nm; flow rate: 1 ml/min; retention time: 4.17 minutes HPLC 2: Column C$_{10}$ Si 60 (5 μm) (250 mm×4.0 mm×5μ); mobile phase: hexane:ethyl acetate (90:10); wavelength: 254 nm; flow rate: 1.0 ml/min; retention time: 21.60 minutes IR: OH 3400 cm$^{-1}$–3500 cm$^{-1}$; C=O 1750 cm$^{-1}$ All publications, patents, and patent documents, cited in this application, are incorporated by reference herein, as though individually incorporated by reference. In the case of any inconsistencies, the present disclosure, including any definitions therein, will prevail.

The invention has been described with reference to various specific and preferred embodiments and techniques. However, it should be understood that many variations and modifications may be made while remaining within the spirit and scope of the invention.

The invention claimed is:

1. A process for the stereospecific preparation of an ester of formula (I):

Ph-CH$_2$—CH$_2$—CH(OR$^2$)—COOR$^1$    (I)

wherein R$^1$ is C$_{1-6}$ alkyl; and

R$^2$ is hydrogen, a protecting group or a leaving group wherein the process comprises reacting a nitrile of formula (II):

Ph-CH$_2$—CH$_2$—CH(OH)—CN    (II)

with a solution of an inorganic acid in an alcohol; and wherein * signifies the (R) stereoisomer;

and optional conversion of a compound of formula (I), wherein R$^2$ is H, to the compound of formula (I).

2. The process of claim 1 wherein R$^1$ is ethyl.

3. The process of claim 1, wherein the acid is hydrogen chloride.

4. The process of claim 1, wherein the alcohol is ethanol.

5. The process of claim 1, wherein the reaction is carried out under substantially anhydrous conditions.

6. The process of claim 1, wherein the acid/alcohol solution comprises greater than 7% w/v of the acid, based on the volume of the solution.

7. The process of claim 1, wherein the reaction is carried out at the reflux temperature of the alcohol.

8. The process of claim 1, wherein the reaction is carried out at 70–85° C. and goes to completion in the range of from 12 to 20 hours.

9. The process of claim 1, wherein the ratio of nitrile of formula (II); acid/alcohol solution is in the range of from 1:6 to 1:10, by volume.

10. The process of claim 9, wherein the ratio of nitrile of formula (II); acid/alcohol solution is in about 1:8, by volume.

11. A process for the stereospecific preparation of an ester of formula (I):

Ph-CH$_2$—CH$_2$—CH(OR$^2$)—COOR$^1$    (I)

wherein R$^1$ is C$_{1-6}$ alkyl; and

R$^2$ is hydrogen, a protecting group or a leaving group which process comprises reaction of an imine of formula (III):

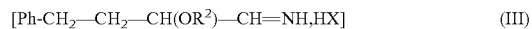

[Ph-CH$_2$—CH$_2$—CH(OR$^2$)—CH=NH,HX]    (III)

wherein R$^2$ is as defined in formula (II); and X is an anion of an inorganic acid, with an alcohol of formula R$^1$OH, wherein R$^1$ is C$_{1-6}$ alkyl.

12. The process of claim 11, wherein R$^1$ is ethyl.

13. The process of claim 11, wherein X is a halide.

14. The process of claim 13, wherein X is chlorine.

15. The process of claim 11, wherein the reaction is carried out under substantially anhydrous conditions.

16. The ester of formula (I), comprising at least 97% of the (R) isomer, wherein the ester is prepared by the process of claim 1.

17. The ester of formula (I), comprising at least 97% of the (R) isomer, wherein the ester is prepared by the process of claim 11.

* * * * *

UNITED STATES PATENT AND TRADEMARK OFFICE
CERTIFICATE OF CORRECTION

PATENT NO.         : 7,094,920 B2                                                    Page 1 of 1
APPLICATION NO.    : 10/719660
DATED              : August 22, 2006
INVENTOR(S)        : Tikare It is certified that error appears in the above-identified patent and that said Letters Patent is hereby corrected as shown below:

In column 1, line 18, delete "'prls'" and insert -- 'prils' --, therefor.

In column 2, line 44, delete "(I)" and insert -- (II) --, therefor.

In column 3, line 5, delete "add" and insert -- acid --, therefor.

In column 5, line 3, delete "T mp" and insert -- Temp. --, therefor.

In column 5, line 3, delete "Tim" and insert -- Time --, therefor.

Signed and Sealed this

Twenty-ninth Day of December, 2009

David J. Kappos
*Director of the United States Patent and Trademark Office*